(12) United States Patent
Hardy et al.

(10) Patent No.: US 11,918,680 B2
(45) Date of Patent: Mar. 5, 2024

(54) CLEANSING COMPOSITIONS

(71) Applicant: Colgate-Palmolive Company, New York, NY (US)

(72) Inventors: Eugene Hardy, Old Bridge, NJ (US); Shujiang Cheng, Warren, NJ (US); Zeenat Nabi, Cranbury, NJ (US); Jeffrey Mastrull, Flemington, NJ (US); Evangelia Arvanitidou, Princeton, NJ (US); Laurence Du-Thumm, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 177 days.

(21) Appl. No.: 17/304,578

(22) Filed: Jun. 23, 2021

(65) Prior Publication Data

US 2021/0322295 A1    Oct. 21, 2021

Related U.S. Application Data

(63) Continuation of application No. 16/065,974, filed as application No. PCT/US2016/069370 on Dec. 30, 2016, now abandoned.

(60) Provisional application No. 62/273,789, filed on Dec. 31, 2015.

(51) Int. Cl.
| | |
|---|---|
| A61K 8/42 | (2006.01) |
| A61K 8/44 | (2006.01) |
| A61K 8/46 | (2006.01) |
| A61K 8/81 | (2006.01) |
| A61Q 19/10 | (2006.01) |

(52) U.S. Cl.
CPC ............. *A61K 8/8164* (2013.01); *A61K 8/42* (2013.01); *A61K 8/44* (2013.01); *A61K 8/442* (2013.01); *A61K 8/463* (2013.01); *A61K 8/466* (2013.01); *A61K 8/8182* (2013.01); *A61Q 19/10* (2013.01); *A61K 2800/596* (2013.01)

(58) Field of Classification Search
None
See application file for complete search history.

(56) References Cited

U.S. PATENT DOCUMENTS

| | | |
|---|---|---|
| 4,976,315 A | 12/1990 | Prukop et al. |
| 5,310,508 A | 5/1994 | Subramanyam et al. |
| 5,922,346 A | 7/1999 | Hersh |
| 6,303,656 B1 | 10/2001 | Burnier |
| 6,635,607 B2 | 10/2003 | Queen et al. |
| 6,656,499 B1 | 12/2003 | Foldvari et al. |
| 7,378,479 B2 | 5/2008 | Barker et al. |
| 7,473,673 B2 | 1/2009 | Polonka et al. |
| 8,048,921 B2 | 11/2011 | Kramer et al. |
| 8,808,670 B2 | 8/2014 | Doring et al. |
| 9,682,027 B2 | 6/2017 | Prencipe et al. |
| 2004/0241114 A1 | 12/2004 | Gupta |
| 2005/0238679 A1 | 10/2005 | Biergiesser et al. |
| 2006/0127342 A1 | 6/2006 | Levis |
| 2006/0228317 A1 | 10/2006 | Chrisstoffels et al. |
| 2009/0202450 A1 | 8/2009 | Prencipe et al. |
| 2010/0316580 A1 | 12/2010 | Kohli et al. |
| 2013/0022687 A1 | 1/2013 | Fitzgerald, Jr. et al. |
| 2013/0217748 A1 | 8/2013 | Sartingen et al. |

FOREIGN PATENT DOCUMENTS

| | | |
|---|---|---|
| EA | 201100242 | 8/2011 |
| EP | 0592073 | 5/1996 |
| EP | 1337233 | 8/2003 |
| EP | 1579847 | 9/2005 |
| EP | 1586307 | 11/2005 |
| EP | 1721601 | 11/2006 |
| EP | 1935395 | 6/2008 |
| EP | 2054020 | 5/2009 |
| EP | 2462919 | 6/2015 |
| FR | 2939030 | 6/2010 |
| RU | 2469701 | 12/2012 |
| RU | 2543656 | 3/2015 |
| WO | 1998/018432 | 5/1998 |
| WO | 2010/052329 | 5/2010 |
| WO | 2010/060729 | 6/2010 |
| WO | 2011/130460 | 10/2011 |
| WO | 2014/095617 | 6/2014 |
| WO | 2014/191117 | 12/2014 |
| WO | 2015/024567 | 2/2015 |

OTHER PUBLICATIONS

Amource, 2015, "Hand Cream," Mintel GNPD Database AN: 3539953.
Douglas Cosmetics, 2014, "Anti-Dandruff Shampoo," 2014, Database Mintel GNPD AN: 2838697.
International Search Report and Written Opinion of the International Searching Authority in International Application No. PCT/US2016/069370, dated May 30, 2017.
Philip B, 2013, "Nordic Wood Hair & Body Shampoo," Database Mintel GNPD AN: 2047789.

*Primary Examiner* — Katherine Peebles

(57) ABSTRACT

Described herein, are personal care compositions comprising a surfactant system; an amino acid, e.g. taurine; and a deposition aid comprising a PVM/MA copolymer having a M.W. of from about 30,000 to about 1,000,000, or a vinylimidazolium vinyl pyrrolidone copolymer. Methods of making and using these compositions are also described.

7 Claims, No Drawings

CLEANSING COMPOSITIONS

BACKGROUND

The use of taurine and other similar benefit agents in cosmetic and antibacterial personal care liquid cleansing compositions has grown recently. However, there are challenges in delivering significant levels of taurine and other benefit agents that can provide preferred and meaningful benefits to the skin.

There is also a need for the proper selection and use of deposition aids at particular ratios that can maintain other important physical performance properties and acceptable long-term product stability at standard aging conditions for the preferred liquid cleansing product. Embodiments of the present invention are designed to meet these, and other, needs.

BRIEF SUMMARY

Compositions, methods of use, and methods of production for personal care compositions are provided herein. Safe and effective personal care compositions are also provided.

It has been found that that when certain PVM/MA copolymers, or a vinylimidazolium vinyl-2-pyrrolidone copolymer, are incorporated into a personal care composition containing an anionic or compatible cationic-based surfactant system, the corresponding personal care composition can deliver taurine or other benefit agents to the skin while providing a required balance of formulation properties. Specifically, the compositions herein provide for enhanced delivery of a benefit agent while delivering other preferred foam, sensory profile and antibacterial efficacy, and formula stability at a variety of storage conditions.

In a first exemplary embodiment, the present disclosure provides a personal care composition comprising: a surfactant system; an amino acid, e.g., taurine or arginine; and a deposition aid comprising a PVM/MA copolymer having a molecular weight (M.W.) of from about 30,000 to about 1,000,000, or a vinylimidazolium vinyl-2-pyrrolidone copolymer.

In a second exemplary embodiment, the present disclosure provides a method for increasing the deposition of an amino acid, e.g., taurine or arginine, onto mammalian skin surface from a personal care composition, comprising the steps of formulating a personal care composition to include taurine and a deposition aid comprising a PVM/MA copolymer having a M.W of from about 30,000 to about 1,000,000, or a vinylimidazolium vinyl-2-pyrrolidone copolymer, and applying the composition to the skin of a mammal.

In a third exemplary embodiment, the present disclosure provides a method for the preparation of a personal care composition comprising combining together in a personal care composition base: a surfactant system comprising at least one anionic surfactant, at least one zwitterionic surfactant, and at least one nonionic surfactant; an amino acid, e.g., taurine or arginine; and a deposition aid comprising a PVM/MA copolymer having a M.W. of from about 30,000 to about 1,000,000, or a vinylimidazolium vinyl-2-pyrrolidone copolymer.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. Unless otherwise indicated, the amounts of material given herein are based on the weight of active material.

The present disclosure provides personal care compositions comprising a surfactant system; taurine; and a deposition aid comprising a PVM/MA copolymer having a M.W. of 30,000 to about 1,000,000, or a vinylimidazolium vinyl-2-pyrrolidone copolymer. In some embodiments, the personal care compositions further include one or more further active agents, such as skin lubricants, analgesics, conditioners, and antibacterial agents.

In one exemplary embodiment, the present disclosure provides a personal care composition (Composition 1) comprising a surfactant system; an amino acid, and a deposition aid comprising a PVM/MA copolymer having a molecular weight (M.W.) of from about 30,000 to about 1,000,000, e.g. about 300,000 to about 800,000, or a vinylimidazolium vinyl pyrrolidone copolymer.

The present disclosure provides additional exemplary embodiments, including:

1.1 Composition 1, wherein the amino acid comprises an amino group and a sulfonic acid group; e.g., taurine.
1.2 Composition 1, wherein the amino acid comprises an amino group and a carboxy group; e.g., arginine or glycine.
1.3 Composition 1, wherein the amino acid is selected from taurine, arginine, glycine, and combinations of one or more thereof.
1.4 Composition 1, wherein the amino acid is or comprises taurine.
1.5 Any Composition 1 or 1.1-1.4, wherein the PVM/MA copolymer comprises a 1:4 to 4:1 copolymer of maleic anhydride or acid with a further polymerizable ethylenically unsaturated monomer; for example 1:4 to 4:1, e.g. about 1:1.
1.6 Any Composition 1 or 1.1-1.4, wherein the further polymerizable ethylenically unsaturated monomer comprises methyl vinyl ether (methoxyethylene); and optionally has a molecular weight of about 700,000; and optionally is a liquid at room temperature.
1.7 Any Composition 1 or 1.1-1.4, wherein the PVM/MA copolymer comprises a copolymer of methyl vinyl ether/maleic anhydride, wherein the anhydride is hydrolyzed following co-polymerization to provide the corresponding acid;
1.8 Any Composition 1 or 1.1-1.4, wherein the PVM/MA copolymer comprises a GANTREZ® polymer, for example GANTREZ® S-96 polymer
1.9 Any Composition 1 or 1-1.4, wherein the vinylimidazolium vinyl-2-pyrrolidone copolymer is a vinylimidazolium vinyl pyrrolidone copolymer, for example 1-methyl-3-vinylimidazolium methyl sulfate-N-vinyl-2-pyrrolidone copolymer, also known as Polyquaternium 44.

1.10 Any Composition 1 or 1.1-1.9, wherein the deposition aid is present in the composition in an amount of from 0.01% to 2%, for example from 0.01% to 1%, for example from 0.03% to 1%, for example from 0.05% to 0.08%, for example from 0.06% to 0.07%, by weight of the composition.

1.11 Any Composition 1 or 1.1-1.10, wherein the surfactant system comprises at least one anionic surfactant; at least one zwitterionic surfactant; and at least one nonionic surfactant.

1.12 Any Composition 1 or 1.1-1.11, wherein the surfactant system is present in the composition in an amount of from 5% to 30%, for example from 5% to 25%, for example from 10% to 20%, for example from 12% to 18%, for example from 14% to 16%, by weight of the composition 1.13 Any Composition 1 or 1.1-1.12, wherein the surfactant system comprises an anionic surfactant selected from sulfate surfactants; for example sodium laureth sulfate, alpha olefin sulfate, sodium lauryl sarcosinate, sodium pareth sulfate, sodium myreth sulfate, sodium dodecyl sulfate, ammonium lauryl sulfate, and ammonium laureth sulfate; and sulfonate surfactants, for example alkyl sulfonates and alpha olefin sulfonates.

1.14 Any Composition 1 or 1.1-1.13, wherein the surfactant system comprises a zwitterionic surfactant selected from quaternary ammonium carboxylate betaines, for example cocoamidopropyl betaine, and sultaines including cocamidopropylhydroxysultaine.

1.15 Any Composition 1 or 1.1-1.14. wherein the surfactant system comprises one or more nonionic surfactants independently selected from polyether surfactants (e.g., PPG-2 hydroxyethyl cocamide), alcohol ethoxylate surfactants (e.g., C12-16 alcohol EO 7:1), fatty acid amide surfactants (e.g., cocamide MEA), and polyoxy ethers of alcohols (e.g., laureth-10), condensation products of aliphatic (C8-C18) primary or secondary linear branched chain alcohols with alkylene oxides or phenols with alkylene oxides, ethylene oxides and having from 6- to 30 ethylene oxide groups; fatty acid alkanolamides including those having 10-18 carbons, such as for example, coconut fatty acid monoethanolamide and coco mono-isopropanolamide.

1.16 Any Composition 1 or 1.1-1.15, wherein the anionic surfactant is present in the composition in an amount of from 1% to 15%, for example from 2% to 12%, for example from 6% to 10%, for example from 7% to 10%, for example from 8% to 9%, by weight of the composition.

1.17 Any Composition 1 or 1.1-1.16, wherein the surfactant system comprises sodium laureth sulfate.

1.18 Any Composition 1 or 1.1-1.16, wherein the zwitterionic surfactant comprises one or both of cocamidopropyl betaine and oleamidopropyl betaine.

1.19 Any Composition 1 or 1.1-1.17, wherein the zwitterionic surfactant comprises cocamidopropyl betaine.

1.20 Any Composition 1 or 1.1-1.19, wherein the surfactant system comprises at least one anionic surfactant; at least one zwitterionic surfactant; and at least one nonionic surfactant; wherein:
  a. the at least one anionic surfactant is selected from sulfate surfactants, for example sodium laureth sulfate;
  b. the at least one zwitterionic surfactant is selected from quaternary ammonium carboxylate betaines, for example cocoamidopropyl betaine; and
  c. the at least one nonionic surfactant is selected from polyether surfactants, alcohol ethoxylate surfactants, fatty acid amide surfactants, and polyoxy ethers of alcohols.

1.21 Any Composition 1.20, wherein:
  a. the at least one polyether surfactant comprises PPG-2 hydroxyethyl cocamide;
  b. the at least one alcohol ethoxylate surfactant comprises C12-16 alcohol EO 7:1;
  c. the at least one fatty acid amide surfactant comprises cocamide MEA; and
  d. the at least one polyoxy ether of an alcohol comprises laureth-10.

1.22 Any Composition 1 or 1.1-1.21, wherein taurine is present in the composition in an amount of from 0.1% to 5%, for example from 1% to 4%, for example from 2% to 3%, by weight of the composition.

1.23 Any Composition 1 or 1.1-1.122, wherein the taurine and the deposition aid are present in the composition in a respective ratio of from 30:1 to 45:1; or from 35:1 to 42:1; of from 37:1 to 40:1; or from 38:1 to 39:1, by weight of active.

1.24 Any Composition 1 or 1.1-1.23, wherein the composition further comprises one or more further active or inactive ingredients selected from rheology modifiers, skin lubricants, analgesics, preservatives, conditioners, antibacterial agents, chelating agents, emulsifiers, antioxidants, pH regulating agents, thickeners, proteins, plant extracts, perfumes, dyes coloring agents and fragrances.

1.25 Any Composition 1 or 1.1-1.24, wherein the composition comprises one or more amino acids, for example arginine and glycine, for example L-arginine and L-glycine, for example wherein the weight ratio of taurine:arginine:glycine in the composition is:
(2-69):(1-40):(0.5-1.5); (2-15):(1-10):(0.5-1.5); (2-13):(1-7):(0.75-1.25); (2-13):(1-7):(0.9-1.1); (2-13):(1-7):1; (60-69):(25-35):(0.5-1.5); (62-69):(28-35):(0.75-1.25); (64-69):(30-35):(0.9-1.1); (64-69):(30-35):1; 65:34:1 or 69:30:1; and wherein the combined total amount of taurine, arginine and glycine in the composition is from 0.001% to 5% of the composition by weight.

In some embodiments, the present disclosure provides personal care liquid cleansing compositions comprising a surfactant system; an amino acid, e.g., taurine; and a deposition aid comprising a PVM/MA copolymer having a molecular weight (M.W.) of about 30,000 to about 1,000,000, e.g. about 300,000 to about 800,000, or a vinylimidazolium vinyl pyrrolidone copolymer. It has been discovered in accordance with the present disclosure that the PVM/MA copolymer or vinylimidazolium vinyl pyrrolidone copolymer affords enhanced delivery of benefit aids such as taurine, while also delivering the desired foaming and sensory profile, as well as providing efficacy of actives such as antibacterial agents, and formula stability in a variety of storage conditions.

The term "PVM/MA copolymer" as used herein is intended to include copolymers of maleic anhydride or acid with another polymerizable ethylenically unsaturated monomer, preferably methyl vinyl ether/maleic anhydride. In some embodiments, the copolymers include 1:4 to 4:1 copolymers of maleic anhydride or acid with another polymerizable ethylenically unsaturated monomer, e.g., methyl vinyl ether (methoxyethylene), having a molecular weight (M.W.) of about 30,000 to about 1,000,000; for example 1:4 to 4:1, e.g. about 1:1, copolymers of methyl vinyl ether/maleic anhydride, wherein the anhydride is hydrolyzed following co-polymerization to provide the corresponding acid, having a molecular weight (M.W.) of about 30,000 to about 900,000, e.g. about 300,000 to about 800,000, e.g., as sold under the trade name GANTREZ®. Representative useful GANTREZ® copolymers include, e.g., GANTREZ® AN 139 (M.W. 500,000), AN 119 (M.W. 250,000), and GANTREZ® S-96 Pharmaceutical Grade (M.W. 700,000) available from Ashland Specialty Chemicals, Bound Brook, N.J. 08805. In some embodiments, the PVM/MA copolymer is GANTREZ® S-96 Pharmaceutical Grade.

In some embodiments, the vinylimidazolium vinyl pyrrolidone copolymer is a vinylimidazolium vinyl-2-pyrrolidone copolymer, for example 1-methyl-3-vinylimidazolium methyl sulfate-N-vinyl-2-pyrrolidone copolymer, CAS No. 150599-70-5, also known as Polyquaternium 44, sold by Dewolf Chemical Co. under the name Luviquat Ultracare AT 1.

In some embodiments, the PVM/MA copolymer, or the vinylimidazolium vinyl pyrrolidone copolymer, or combination thereof, is present in the personal care liquid cleansing compositions of the disclosure in a combined amount of from 0.01% to 2%, for example from 0.01% to 1%, for example from 0.03% to 1%, for example from 0.05% to 0.08%, for example from 0.06% to 0.07%, by weight of the composition.

In some embodiments, the personal care compositions of the present invention comprise an effective amount of an antibacterial agent. In some embodiments, the antibacterial agent is present in the amount of about 0.01 wt % to about 10 wt % of the personal care composition. In some embodiments, the antibacterial agent is present in the amount of about 0.15 wt % of the personal care composition.

In some embodiments, the personal care compositions include a surfactant system that comprises at least two surfactants, optionally at least three surfactants. In some embodiments, the surfactant system includes at least one anionic surfactant; at least one zwitterionic surfactant; and at least one nonionic surfactant. In some embodiments, the surfactant system can comprise from 5% to 30%, for example from 5% to 25%, for example from 10% to 20%, for example from 12% to 18%, for example from 13% to 17%, for example from 14% to 16% of the composition by weight.

Anionic surfactants useful herein include the water-soluble salts of alkyl sulfates and sulfonates, and alkyl ether sulfates and sulfonates having from 8 to 20 carbon atoms in the alkyl radical (e.g., sodium alkyl sulfate) and the water-soluble salts of sulfonated monoglycerides of fatty acids having from 8 to 20 carbon atoms. Sodium laurel ether sulfate (SLES; sodium laureth sulfate), sodium lauryl sulfate and sodium coconut monoglyceride sulfonates are examples of anionic surfactants of this type. Further examples of suitable sulfate surfactants include alpha olefin sulfate, sodium pareth sulfate, sodium myreth sulfate, sodium dodecyl sulfate, ammonium lauryl sulfate, and ammonium laureth sulfate, and sulfonate surfactants, for example alkyl sulfonates and alpha olefin sulfonates. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Generally, the anionic surfactant is present in the composition in an amount of from 1% to 15%, for example from 2% to 12%, for example from 6% to 10%, for example from 7% to 10%, for example from 8% to 9%, by weight of the composition. In some preferred embodiments, the anionic surfactant includes, or consists of, sodium laurel ether sulfate.

Examples of nonionic surfactants that can be used in the present compositions include those that can broadly be defined as compounds produced by the condensation of alkylene oxide groups (hydrophilic in nature) with an organic hydrophobic compound which may be aliphatic or alkyl-aromatic in nature; for example condensation products of aliphatic (C8-C18) primary or secondary linear branched chain alcohols with alkylene oxides or phenols with alkylene oxides, ethylene oxides and having from 6- to 30 ethylene oxide groups; fatty acid alkanolamides including those having 10-18 carbons, such as for example, coconut fatty acid monoethanolamide and coco mono-isopropanolamide.

Further examples of suitable nonionic surfactants include poloxamers (sold under trade name PLURONIC®), polyoxyethylene, polyoxyethylene sorbitan esters (sold under trade name TWEEN®), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, alkyl polyglycosides (for example, fatty alcohol ethers of polyglycosides, such as fatty alcohol ethers of polyglucosides, e.g., decyl, lauryl, capryl, caprylyl, myristyl, stearyl and other ethers of glucose and polyglucoside polymers, including mixed ethers such as capryl/caprylyl ($C_{8-10}$) glucoside, coco ($C_{8-16}$) glucoside, and lauryl ($C_{12-16}$) glucoside), long chain tertiary amine oxides, long chain tertiary phosphine oxides, long chain dialkyl sulfoxides, and mixtures of such materials.

Examples of some preferred nonionic surfactants that can be used in the present compositions include polyether surfactants such as, for example, PPG-2 hydroxyethyl cocamide, alcohol ethoxylate surfactants such as, for example, C12-16 alcohol EO 7:1, fatty acid amide surfactants such as, for example, cocamide MEA, and polyoxy ethers of alcohols such as, for example, laureth-10. In some embodiments, the nonionic surfactant or surfactants are present in the composition in a total amount of from 1% to 8%, for example from 2% to 6%, for example from 3% to 6%, by weight of the composition.

Zwitterionic surfactants (also known as amphoteric surfactants) that can be used in the present compositions include derivatives of aliphatic secondary and tertiary amines in which the aliphatic radical can be a straight chain or branched and wherein one of the aliphatic substituents contains from 8 to 18 carbon atoms and one contains an anionic water-solubilizing group, e.g., carboxylate, sulfonate, sulfate, phosphate, or phosphonate. Mixtures of zwitterionic surfactants can also be employed. Some preferred zwitterionic surfactants include betaines, and in particular quaternary ammonium carboxylate betaines, which are betaines having a quaternary nitrogen atom cationic group, and a carboxylate anionic group. One preferred zwitterionic surfactant is cocamidopropyl betaine. Further examples of suitable zwitterionic surfactants include sultaines, for example cocamidopropylhydroxysultaine. In some embodiments, the zwitterionic surfactant or surfactants are present in the composition in a total amount of from 1% to 8%, for example from 1% to 6%, for example from 1% to 5%, for example from 2% to 5% m for example from 2% to 4% by weight of the composition.

In some embodiments, the surfactant system comprises at least one anionic surfactant selected from sulfate surfactants; for example sodium laureth sulfate; at least one zwitterionic surfactant selected from quaternary ammonium carboxylate betaines, for example cocoamidopropyl betaine; and at least one nonionic surfactant selected from polyether surfactants, alcohol ethoxylate surfactants, fatty acid amide surfactants, and polyoxy ethers of alcohols. In some such embodiments, the composition includes at least one polyether surfactant, for example PPG-2 hydroxyethyl cocamide; at least one alcohol ethoxylate surfactant, for example C12-16 alcohol EO 7:1; at least one fatty acid amide surfactant, for example cocamide MEA; and at least one polyoxy ether of an alcohol, for example laureth-10.

In some embodiments, the compositions of the present invention provide several benefits, including the enhanced deposition of benefit agents onto a mammalian skin surface. The present compositions find use with a wide variety of benefit agents, including for example skin lubricants, analgesics, conditioners, antibacterial agents, antioxidants, sunscreen agents, keratolytic agents, and the like. In other embodiments, the compositions of the present invention provide enhanced deposition of taurine. In some such embodiments, taurine is present in the composition in an amount of from 0.1% to 5%, for example from 1% to 4%, for example from 2% to 3%, by weight of the composition.

In some embodiments, the amino acid, e.g. taurine, and the deposition aid—i.e., the PVM/MA copolymer having a M.W. of from about 30,000 to about 1,000,000, or the vinylimidazolium vinyl pyrrolidone copolymer—are present in the composition in a weight ratio of from about 3:1 to about 40:1; or from about 3:1 to about 8:1, or from about 4:1 to about 6:1; or from about 30:1 to about 45:1; or from about 35:1 to about 42:1; of from about 37:1 to about 40:1; or from about 38:1 to about 39:1.

In some embodiments, the personal care compositions can include one or more of a variety of optional ingredients, the selection of which can depend in part on the particular properties desired in the composition. Non-limiting examples of such optional ingredients include skin conditioning agents, moisturizing agents, fragrance, coloring agents such as dyes and pigments, titanium dioxide, chelating agents such as EDTA, sunscreen active ingredients such as butyl methoxy benzoylmethane; antiaging compounds such as alpha hydroxy acids, beta hydroxy acids; preservatives such as hydantoins, imidazolines; polyols such as glycerol, sorbitol, propylene glycol and polyethylene glycols; antioxidants such as butylated hydroxytoluene (BHT); vitamins such as A, E, K and C; amino acids; essential oils and extracts thereof such as rosewood and jojoba, particulate matter such as polyethylene beads, jojoba beads, silica, talc, calcium carbonate, lufa, or oat flour, and mixtures of any of the foregoing components.

In some embodiments, in addition to one or more of the additional ingredients above, the personal care compositions can further include one or more active or inactive ingredients selected from rheology modifiers, preservatives, chelating agents, emulsifiers, antioxidants, alpha hydroxy acids, and pH regulating agents. For example, in some embodiments, the cleansing compositions of the disclosure include fragrance in an amount of about 0.001% to about 2% by weight of the composition.

The amino acids useful in the present invention include but are not limited to amino acids, for example alpha amino acids, having an amino (—$NH_2$) group and a carboxyl (—COOH) group, and amino acids having an amino group and a sulfonic acid (—$SO_3H$)) group. Examples of the former include the amino acids alanine, arginine, asparagine, aspartic acid, cyteine, glutamine, glutamic acid, glycine, histidine, isoleucine, leucine, lysine, methionine, phenylalanine, proline, serine, threonine, tryptophan, tyrosine and valine, preferably in the L-form. Examples of the latter include taurine and the lower (e.g., $C_3$-$C_6$) amino alkyl sulfonic acids.

In some embodiments, the personal care compositions include more than one amino acid, for example and not limitation taurine and one or more additional amino acids. Examples of preferred amino acids include arginine and glycine, preferably L-glycine and L-arginine. In some embodiments, the arginine and glycine enhance the barrier repair function of the skin and also reduce skin irritation and inflammation. Furthermore, it has unexpectedly been found that the effect of taurine is synergistically enhanced in the presence of arginine and glycine.

Accordingly, in some embodiments, the present invention provides compositions comprising taurine, and further comprising arginine and glycine, for example L-arginine and L-glycine, in a weight ratio of taurine:arginine:glycine in the composition of (2-69):(1-40):(0.5-1.5); (2-15):(1-10):(0.5-1.5); (2-13):(1-7):(0.75-1.25); (2-13):(1-7):(0.9-1.1); (2-13):(1-7):1; (60-69):(25-35):(0.5-1.5); (62-69):(28-35):(0.75-1.25); (64-69):(30-35):(0.9-1.1); (64-69):(30-35):1; 65:34:1 or 69:30:1. In some such embodiments, the combined total amount of taurine, arginine and glycine in the composition is from 0.001% to 5% of the composition by weight.

In some embodiments, the cleansing compositions of the disclosure include one or more pigments, for example in an amount of about 0.001% to about 1% by weight.

In some embodiments, the personal care compositions of the disclosure include one or more alpha hydroxy acids, for example citric acid, for example in an amount of about 0.001% to about 1% by weight.

In some embodiments, the personal care compositions of the disclosure include one or more conditioning agents, for example polyquaternium 7, for example in an amount of about 0.001% to about 1% by weight.

In some embodiments, the personal care compositions of the disclosure include one or more preservatives, for example methylparaben, propylparaben or sodium benzoate, for example in an amount of about 0.001% to about 1% by weight.

In some embodiments, the personal care compositions of the disclosure include one or more of inorganic salts (e.g., sodium chloride, sodium sulfate), brighteners, perfumes, colorants, sequestering agents, opacifiers, chelating agents (e.g., EDTA), humectants (e.g., polyols, for example, glycerol), or any combination thereof.

In some embodiments, the personal care composition comprises a bar soap. In some embodiments, the bar soap includes free fatty acids to provide enhanced skin feel benefits, such as softer or smoother feeling skin. Suitable free fatty acids include those derived from tallow, coconut oil, palm oil and palm kernel oil. Free oil is also suitable.

In a second exemplary embodiment, the invention includes a method (Method 1) of increasing the deposition of an amino acid, e.g. taurine, onto mammalian skin surface from a personal care composition, comprising the steps of formulating a personal care composition to include taurine and a deposition aid comprising a PVM/MA copolymer having a M.W. of from about 30,000 to about 1,000,000, or a vinylimidazolium vinyl pyrrolidone copolymer, and applying the formulation to the skin of a mammal. The present disclosure provides additional exemplary embodiments, including:

1.1 Method 1, wherein the personal care composition is a composition as described above (e.g., any Composition 1 and 1.1-1.25).

In a third exemplary embodiment, the invention includes a method (Method 2) for the preparation of a personal care composition comprising combining together in a personal care composition base: a surfactant system comprising at least one anionic surfactant, at least one zwitterionic surfactant, and at least one nonionic surfactant; an amino acid, e.g. taurine; and a deposition aid comprising a PVM/MA copolymer having a M.W. of from about 30,000 to about 1,000,000, or a vinylimidazolium vinyl pyrrolidone copolymer, or a combination of both.

In a fourth exemplary embodiment, the invention includes a method (Method 3) of cleansing a skin surface comprising providing a personal care composition as described above (e.g., any Composition 1 and 1.1-1.25); and applying the composition to the skin.

In a fifth exemplary embodiment, the invention includes a method (Method 4) for reducing a population of bacteria on a skin surface, comprising contacting the skin surface with a personal care composition as described above (e.g., any Composition 1 and 1.1-1.25).

The compositions herein can be prepared by procedures known in the art. In general, the various components of the composition are combined with water and mixed to uniformity. Premixes can be employed to pre-disperse or pre-dissolve components, and in particular, powder components, and/or to add several components simultaneously.

Exemplary embodiments of the present disclosure will be illustrated by reference to the following examples, which are included to exemplify, but not limit the scope of, the present invention.

EXAMPLES

Example 1

The compositions of the Examples below are prepared by techniques known by those of skill in the art. In some compositions it may be advantageous to add one surfactant prior to another, for example adding in order, anionic (e.g., SLES), then zwitterionic (e.g., Cocamidopropyl Betaine), and then nonionic (e.g. Cocomonoethanolamide and/or PPG-2 Hydroxyethyl cocamide) surfactants.

Table 1 (below) describes two exemplary compositions of the present invention (Formula 1 and Formula 2) and two comparative compositions (Comparative Formula A and Comparative Formula B).

TABLE 1

| Ingredient | Formula 1 | Formula 2 | Comparative Formula A % AI | Comparative Formula B |
|---|---|---|---|---|
| Water | QS | QS | QS | QS |
| SLES | 8.30 | 8.30 | 8.30 | 8.30 |
| Cocamidopropyl Betaine | 2.53 | 2.53 | 2.53 | 2.53 |
| Antibacterial (Trichlocarban) | 0.15 | 0.15 | 0.15 | 0.15 |
| Cocomonoethanolamide | 0.55 | 0.55 | 0.55 | 0.55 |
| Glycerin | 0.10 | 0.10 | 0.10 | 0.10 |
| Taurine | 2.50 | 2.50 | 2.50 | 2.50 |
| PVM/MA Copolymer (Gantrez S-96) | 0.50 | — | — | — |
| PVM/MA Copolymer (Gantrez S-97) | — | — | — | 0.50 |

TABLE 1-continued

| Ingredient | Formula 1 | Formula 2 | Comparative Formula A % AI | Comparative Formula B |
|---|---|---|---|---|
| Polyquaternium-44 | — | 0.50 | — | — |
| Fragrance | 1.00 | 1.00 | 1.00 | 1.00 |
| PPG-2 hydroxyethyl Cocamide | 0.92 | 0.92 | 0.92 | 0.92 |
| Ethoxylated Fatty alcohol | 0.92 | 0.92 | 0.92 | 0.92 |
| Citric Acid | 0.20 | 0.20 | 0.20 | 0.20 |
| NaCl | 0.75 | 0.75 | 0.75 | 0.75 |
| Pearlizer | 1.33 | 1.33 | 1.33 | 1.33 |
| Tetrasodium EDTA 39% Soln. | 0.12 | 0.12 | 0.12 | 0.12 |
| Sodium Benzoate | 0.28 | 0.28 | 0.28 | 0.28 |
| Sodium Salicylate | 0.30 | 0.30 | 0.30 | 0.30 |
| Polyquaternium-7 | 0.20 | 0.20 | 0.20 | 0.20 |

Example 2

The compositions described in Table 1 (above) are evaluated for their ability to maintain viscosity and uniformity at various storage temperatures. After four weeks at 25° C. in high density polyethylene (HDPE) and glass sample jars, Formulas 1 and 2, and Comparative Formula A were found to be acceptable, with no separation. However, Comparative Formula B was found to be unacceptable, with separation observed.

Example 3

In-vivo deposition evaluations are conducted for Formula 1 and Comparative Formula A using a panel of six people. Example 1, which contains a PVM/MA copolymer having a M.W. of from about 30,000 to about 1,000,000, delivers 30% more taurine to the skin of the test subjects than Comparative Formula A, which does not contain a PVM/MA Copolymer.

These results confirm that the presence of a PVM/MA copolymer having a M.W. of from about 30,000 to about 1,000,000 provides enhanced delivery of the benefit agent (e.g. taurine) to the skin.

Example 4

In vitro skin is treated with personal care compositions including the following ingredients:

TABLE 2

| Ingredient | Formula 3 | Formula 4 | Formula 5 % AI | Formula 6 |
|---|---|---|---|---|
| Water | QS | QS | QS | QS |
| SLES | 8.30 | 8.30 | 8.30 | 8.30 |
| Cocamidopropyl Betaine | 2.53 | 2.53 | 2.53 | 2.53 |
| Antibacterial | 0.15 | 0.15 | 0.15 | 0.15 |
| Cocomonoethanolamide | 0.52 | 0.52 | 0.52 | 0.52 |
| Glycerin | 0.10 | 0.10 | 0.10 | 0.10 |
| Taurine | 1.00 | 2.50 | 1.00 | 2.50 |
| PVM/MA Copolymer (Gantrez S-96) | — | — | 0.50 | 0.50 |
| Fragrance | 1.00 | 1.00 | 1.00 | 1.00 |
| PPG-2 hydroxyethyl Cocamide | 0.92 | 0.92 | 0.92 | 0.92 |
| Ethoxylated Fatty alcohol | 0.92 | 0.92 | 0.92 | 0.92 |
| Citric Acid | 0.20 | 0.20 | 0.20 | 0.20 |

TABLE 2-continued

| Ingredient | Formula 3 | Formula 4 % AI | Formula 5 | Formula 6 |
|---|---|---|---|---|
| NaCl | 0.75 | 0.75 | 0.75 | 0.75 |
| Pearlizer | 3.50 | 3.50 | 3.50 | 3.50 |
| Tetrasodium EDTA 39% Soln. | 0.12 | 0.12 | 0.12 | 0.12 |
| Sodium Benzoate | 0.28 | 0.28 | 0.28 | 0.28 |
| Sodium Salicylate | 0.30 | 0.30 | 0.30 | 0.30 |
| Polyquaternium-7 | 0.20 | 0.20 | 0.20 | 0.20 |

The Preparation of VITRO-SKIN samples is adapted from the IMS In Vitro SPF/UVA Protocol for use with Vitro-Skin Substrate, IMS, Inc.

The procedure employs an IMS Hydration chamber that has been thoroughly washed and dried. An 85% DI water/15% glycerin solution is prepared as follows: 256 grams of DI water is added to a 500 ml beaker. 44 grams of glycerin is added and the combination is mixed well (300 g total). Lower volumes of the 85% DI water/15% glycerin solution can be used in needed. The glycerin/water solution is pipetted into the bottom of the hydration chamber. Shelves are placed in the hydration chamber and the lid is applied making sure that it achieves a good seal. Care is applied when removing the lid of the chamber so that it does not tip or splash fluid onto the hydrating vitro-skin. When exposed to constant temperature the system will maintain a controlled humidity environment for hydration of the vitro skin. A control temperature of 23° C. yields optimal results and is maintained for skin hydration purposes.

Hydration of VITRO SKIN

The VITRO-SKIN is carefully removed from its packaging and cut into 2 in×2 in squares using a paper cutter. The film is placed on the shelf/tray inside the humidity chamber, taking care to not overlap the VITRO SKIN pieces. The VITRO SKIN is incubated in the closed, controlled humidity chamber for 16-24 hours prior to product application/deposition studies. The VITRO SKIN should not be left in the hydration chamber for more than 24 hours. The humidity in the chamber is regulated by a solution of 85% water/15% glycerin placed in the bottom of the chamber.

Liquid Cleanser Active Deposition

For each deposition test, it is recommended that the VITRO SKIN pieces be used from the same sheet of VITRO SKIN and be properly hydrated.

Preparation of Liquid Soap Solutions:

5 g of liquid soap are weighed into a labeled Pyrex beaker. 95 g of DI water is added, and the combination is stirred on a stir plate ensuring good mixing, until the solution is uniform. Temperature is ambient. When mixed, 20 ml of the prepared solution is added to a labeled 8 or 16 oz jar (prepared in triplicate). The jars containing the soap solutions are returned to the orbital shaker, which is set at 40° C. setpoint (100 rpm).

Product Application to VITRO SKIN

A VITRO SKIN piece is carefully removed from the Hydration Chamber. The timer is set to appropriate exposure time (1 min). The VITRO SKIN is placed into the jar of soap solution, keeping the "shiny side" up when placing onto the liquid. The timer is started, and the jar is gently swirled and mixed in the orbital shaker at approx. 100 RPM. The VITRO SKIN sample is removed after exposure time using tweezers/forceps and rinsed 10 times in DI water (filled in a 2000 ml-5000 ml beaker). This beaker is rinsed and refilled between test products. The treated VITRO-SKIN sample is placed onto labeled paper towels. The procedure is repeated for other replicates and samples. The treated VITRO SKIN is allowed to dry at ambient conditions for at least 3 hours.

Extraction Procedure

Using tweezers/forceps to hold a piece of VITRO SKIN, each piece is carefully cut into approximately 9-16 small pieces. The cuttings are collected on filter paper, and then put into a labeled scintillation vials. The procedure is repeated for all replicates/test samples. 5 ml of ethanol is added to each sample, and the skin-ethanol vial is Vortexed well. The sample lids are closed, and the VITRO SKIN/ethanol solution is allowed to sit for 48 hours to extract the analyte from the VITRO SKIN (shorter exposure times can lead to high variability). The ethanol is removed from the vials using disposable glass pipettes and as much of the ethanol extraction as possible is transferred into a labeled Kimble Tube. The ethanol is evaporated from the tubes either overnight (open caps to ambient air) or with an evaporator (Genevac), and the samples are capped and ready for reconstitution with controlled volumes of solvent and subsequent HPLC analysis. Note the product used for application should also be measured for original product analyte content.

HPLC Analysis of VITRO SKIN Extraction 300 microliters (μL) of ethanol are added to each labeled Kimble tube, and the tubes are Vortexed well for 2 minutes. Each extraction is filtered into HPLC Vials. 6 point calibration curves of analyte are prepared, and each sample is analyzed using the following HPLC Detection settings:

Mobile phase=depending on desired analyte to be analyzed

Lambda=depending on desired analyte to be analyzed

Flow rate=1.0/min,-typically

Column=C18-typically

Retention time=depending of desired analyte to be analyzed.

Cover the areas under the curves detected to ppm (ug/ml) using the calibration curve. The obtained level of analyte detected in ppm is then coverted to relative deposition per square centimeter of VITRO SKIN $$D_{relative} = \frac{[DT*DF]\left(1g\frac{1g}{100000\ ug}\right)}{A_{VitroSKin}}$$

Where:

$D_{relative}$=Relative Deposition of analyte in g/cm²

$D_T$=Total Deposition from the VITRO SKIN in ppm (ug/ml)

DF=Dilution Factor=Volume of the ethanol added to each sample=0.3 ml in this example $A_{Vitro\ Skin}$=Area of VITRO SKIN calculated as the samples length*height*2 (for both sides). For a 5 cm×5 cm sample=5*5*2=50 cm²

The results are shown below in Table 3 (which is the average of three trials):

TABLE 3

| Formulation | Gantrez S-96 (wt. %) | Taurine (wt. %) | Taurine Deposition (mg) |
|---|---|---|---|
| Formula 3 | 0 | 1.0 | 0.007 |
| Formula 4 | 0 | 2.5 | 0.020 |
| Formula 5 | 0.50 | 1.0 | 0.010 |
| Formula 6 | 0.50 | 2.5 | 0.052 |

It can be seen from these data that greater taurine deposition is observed with the deposition enhancer, and this effect is more pronounced at higher taurine dosing levels. Increasing taurine concentration by 150% in the absence of deposition enhancer (Formulas 3 and 4) increased taurine deposition by approximately 185%; whereas increasing taurine concentration by 150% in the presence of deposition enhancer (Formulas 3 and 4) increased deposition by approximately 420%.

Example 5

The effect of increasing concentration of deposition enhancing agent Gantrez S-96 was determined by in vitro skin as described above with the composition for Formula 4, and similar formulations having the amounts of Gantrez S-96 and/or taurine shown below in Table 4:

TABLE 4

(data are the average of three trials)

| Formulation | Gantrez S-96 (wt. %) | Taurine (wt. %) | Taurine Deposition (mg) |
|---|---|---|---|
| Formula 4 | 0 | 2.5 | 0.020 |
| Formula 7 | 0.50 | 2.5 | 0.052 |
| Formula 8 | 0.75 | 2.5 | 0.055 |
| Formula 9 | 1.0 | 2.5 | 0.065 |

It can be seen from these data that increasing the concentration of deposition aid Gantrez S-96 does not significantly enhance the deposition of taurine.

Example 6

The efficacy of the alternate deposition aid Polyquaternium-44 was determined by the method of Example 4 above. The result is shown below in Table 5:

TABLE 5

(data are the average of three trials)

| Formulation | Polyquaternium-44 (wt. %) | Taurine (wt. %) | Taurine Deposition (mg) |
|---|---|---|---|
| Formula 4 | 0 | 2.5 | 0.020 |
| Formula 10 | 0.50 | 2.5 | 0.066 |

It can be seen that Polyquaternium-44 provides significant deposition enhancement of taurine to the skin surface.

Example 7

The deposition of another amino acid (arginine) was determined for deposition aids Gantrez S-96 and polyquaternium-44 using a personal care composition as described in Table 6 below, including the following ingredients:

TABLE 6

| Ingredient | Formula 11 | Formula 12 % AI | Formula 13 |
|---|---|---|---|
| Water | QS | QS | QS |
| SLES | 8.30 | 8.30 | 8.30 |
| Cocamidopropyl Betaine | 2.53 | 2.53 | 2.53 |
| Antibacterial | 0.15 | 0.15 | 0.15 |
| Cocomonoethanolamide | 0.52 | 0.52 | 0.52 |
| Glycerin | 0.10 | 0.10 | 0.10 |
| Taurine | 1.625 | 1.625 | 1.625 |
| Glycine | 0.025 | 0.025 | 0.025 |
| Arginine | 0.85 | 0.85 | 0.85 |
| PVM/MA Copolymer (Gantrez S-96) | — | — | 0.50 |
| PPG-2 hydroxyethyl Cocamide | 0.92 | 0.92 | 0.92 |
| Ethoxylated Fatty alcohol | 0.92 | 0.92 | 0.92 |
| Acusol OP 301 Opacifier | 0.10 | 0.10 | 0.10 |
| Polyquaternium-44 | — | 0.50 | — |
| Fragrance | 1.10 | 1.10 | 1.10 |
| Citric Acid | 0.25 | 0.25 | 0.25 |
| NaCl | 1.00 | 1.00 | 1.00 |
| Tetrasodium EDTA 39% Soln. | 0.12 | 0.12 | 0.12 |
| Sodium Benzoate | 0.32 | 0.32 | 0.32 |
| Sodium Salicylate | 0.28 | 0.28 | 0.28 |
| Polyquaternium-7 | 0.10 | 0.10 | 0.10 |

The results are shown below in Table 7:

TABLE 7

(data are the average of three trials)

| Formulation | Gantrez S-96 (wt. %) | Polyquaternium-44 (wt. %) | Arginine (wt. %) | Glycine (wt. %) | Taurine (wt. %) | Arginine Deposition (mg) |
|---|---|---|---|---|---|---|
| Formula 11 | 0 | 0 | 0.85 | 0.025 | 1.62 | n.d. |
| Formula 12 | 0 | 0.50 | 0.85 | 0.025 | 1.62 | 0.009 |
| Formula 13 | 0.50 | 0 | 0.85 | 0.025 | 1.62 | 0.0037 | n.d. = not detectable

It can be seen from these data that both deposition aids Gantrez and Polyquaternium-44 enhanced the deposition of arginine. The deposition of glycine was not determined because the concentration of glycine was below the detection limit of the analytical technique.

What is claimed is:

1. A personal care composition comprising a bar soap, wherein the personal care composition comprises:
    a combination of taurine, arginine, and glycine; and
    sodium lauryl ether sulfate, cocamidopropyl betaine, triclocarban, cocomonoethanolamide, glycerin, PPG-2 hydroxyethyl cocamide, ethoxylated fatty alcohol, opacifier, citric acid, NaCl, pearlizer, tetrasodium EDTA, sodium benzoate, sodium salicylate, and 1-methyl-3-vinylimidazolium methyl sulfate-N-vinyl-2-pyrrolidone copolymer (Polyquaternium 44).

2. The personal care composition of claim 1, wherein the 1-methyl-3-vinylimidazolium methyl sulfate-N-vinyl-2-pyrrolidone copolymer (Polyquaternium 44) is present in the composition in an amount of from 0.01% to 2%, or from 0.01% to 1%, or from 0.03% to 1%, or from 0.05% to 0.08%, or from 0.06% to 0.07%, by weight of the composition.

3. The personal care composition of claim 1, wherein the composition comprises sodium lauryl ether sulfate, cocamidopropyl betaine, cocomonoethanolamide, PPG-2 hydroxyethyl cocamide and ethoxylated fatty alcohol in a combined amount of from about 5% to about 30%, or from about 5% to about 25%, or from about 10% to about 20%, or from about 12% to about 18%, or from about 14% to about 16%, by weight of the composition.

4. The personal care composition of claim 1, wherein the sodium lauryl ether sulfate is present in the composition in an amount of from about 1% to about 15%, or from about 2% to about 12%, or from about 6% to about 10%, or from about 7% to about 10%, or from about 8% to about 9%, by weight of the composition.

5. The personal care composition of claim 1, wherein the combination of taurine, arginine, and glycine is are present in the composition in an amount from 0.001% to 5% by weight of the composition.

6. The personal care composition of claim 1, wherein the taurine, arginine, and glycine are present in the composition in a weight ratio of 65:34:1.

7. The personal care composition of claim 1, wherein the personal care composition further comprises one or more additional active or inactive ingredients selected from rheology modifiers, skin lubricants, analgesics, preservatives, conditioners, antibacterial agents, chelating agents, emulsifiers, antioxidants, pH regulating agents, thickeners, proteins, plant extracts, perfumes, dyes and coloring agents, amino acids and fragrances.

* * * * *